(12) United States Patent
Weston et al.

(10) Patent No.: US 8,784,393 B2
(45) Date of Patent: Jul. 22, 2014

(54) DRESSING

(75) Inventors: Richard Scott Weston, Encinitas, CA (US); Tim DeMuro, Tulsa, OK (US); Paul DeMuro, legal representative, Tulsa, OK (US); Tianning Xu, Duluth, GA (US); Farhad Bybordi, Pompano Beach, FL (US); Edward Yerbury Hartwell, Hull (GB); Derek Nicolini, Brough (GB); Kristian David Hall, Hull (GB)

(73) Assignees: BlueSky Medical Group, Inc., Memphis, TN (US); Smith & Nephew PLC, London (GB)

( * ) Notice: Subject to any disclaimer, the term of this patent is extended or adjusted under 35 U.S.C. 154(b) by 1492 days.

(21) Appl. No.: 12/375,191

(22) PCT Filed: Jul. 25, 2007

(86) PCT No.: PCT/US2007/074374
§ 371 (c)(1),
(2), (4) Date: Jan. 6, 2010

(87) PCT Pub. No.: WO2008/014358
PCT Pub. Date: Jan. 31, 2008

(65) Prior Publication Data
US 2010/0106114 A1 Apr. 29, 2010

Related U.S. Application Data

(60) Provisional application No. 60/833,553, filed on Jul. 26, 2006.

(30) Foreign Application Priority Data

Jul. 2, 2007 (GB) .................................. 0712735.0

(51) Int. Cl.
*A61M 1/00* (2006.01)

(52) U.S. Cl.
USPC .......................................................... 604/319

(58) Field of Classification Search
USPC .......................................................... 604/319
See application file for complete search history.

(56) References Cited

U.S. PATENT DOCUMENTS

| | | | |
|---|---|---|---|
| 3,682,180 A | 8/1972 | McFarlane | |
| 3,713,622 A | 1/1973 | Dinger | |

(Continued)

FOREIGN PATENT DOCUMENTS

| | | |
|---|---|---|
| CA | 1320888 | 8/1993 |
| CA | 2198243 A1 | 2/1996 |

(Continued)

OTHER PUBLICATIONS

U.S. Appl. No. 10/652,200, filed Aug. 28, 2003, Richard S. Weston.

(Continued)

*Primary Examiner* — Tatyana Zalukaeva
*Assistant Examiner* — Ginger T Chapman
(74) *Attorney, Agent, or Firm* — Knobbe Martens Olson & Bear LLP

(57) ABSTRACT

A dressing (30), a grommet (10) and a combination thereof are described for making a dressing for use in locating and retaining conduits and/or tubes used in therapy of a wound is described, the dressing (30) comprising a backing layer (32) having an adhesive coating (34) thereon for adhering the dressing (30) to a patient; the backing layer (32) having a cut-out (48) therein for receiving a grommet member (10); said grommet member (10) having at least one aperture (14) therethrough for receiving a conduit; and, said grommet member (10) further comprising a flange portion (16) in some embodiments for attaching the grommet member (10) to said adhesive coated backing layer (32).

37 Claims, 7 Drawing Sheets

(56) References Cited

U.S. PATENT DOCUMENTS

| | | | |
|---|---|---|---|
| 3,826,254 A | 7/1974 | Mellor | |
| 4,261,363 A | 4/1981 | Russo | |
| 4,333,468 A | 6/1982 | Geist | |
| 4,382,441 A | 5/1983 | Svedman | |
| 4,392,853 A * | 7/1983 | Muto | 604/171 |
| 4,525,166 A | 6/1985 | Leclerc | |
| 4,543,100 A | 9/1985 | Brodsky | |
| 4,743,232 A * | 5/1988 | Kruger | 604/180 |
| 4,906,233 A | 3/1990 | Moriuchi et al. | |
| 4,941,882 A * | 7/1990 | Ward et al. | 604/180 |
| 4,969,880 A | 11/1990 | Zamierowski | |
| 5,100,396 A | 3/1992 | Zamierowski | |
| 5,160,315 A | 11/1992 | Heinecke et al. | |
| 5,261,893 A | 11/1993 | Zamierowski | |
| 5,527,293 A | 6/1996 | Zamierowski | |
| 5,549,584 A | 8/1996 | Gross | |
| 5,618,556 A | 4/1997 | Johns et al. | |
| 5,636,643 A | 6/1997 | Argenta | |
| 5,645,081 A | 7/1997 | Argenta | |
| 6,117,111 A | 9/2000 | Fleischmann | |
| 6,142,982 A * | 11/2000 | Hunt et al. | 604/313 |
| 6,345,623 B1 | 2/2002 | Heaton et al. | |
| 6,458,109 B1 | 10/2002 | Henley et al. | |
| 6,471,685 B1 | 10/2002 | Johnson | |
| 6,685,681 B2 | 2/2004 | Lockwood et al. | |
| 6,855,135 B2 * | 2/2005 | Lockwood et al. | 604/313 |
| 7,004,915 B2 | 2/2006 | Boynton et al. | |
| 7,070,584 B2 | 7/2006 | Johnson et al. | |
| 7,117,869 B2 | 10/2006 | Heaton et al. | |
| 7,128,735 B2 | 10/2006 | Weston | |
| 7,216,651 B2 | 5/2007 | Argenta et al. | |
| 7,316,672 B1 | 1/2008 | Hunt et al. | |
| 7,381,859 B2 | 6/2008 | Hunt et al. | |
| 7,485,112 B2 | 2/2009 | Karpowicz et al. | |
| 7,534,927 B2 * | 5/2009 | Lockwood et al. | 602/46 |
| 7,611,500 B1 | 11/2009 | Lina et al. | |
| 7,651,484 B2 | 1/2010 | Heaton et al. | |
| 7,670,323 B2 | 3/2010 | Hunt et al. | |
| 7,678,102 B1 * | 3/2010 | Heaton | 604/543 |
| 7,726,560 B2 * | 6/2010 | Mittal et al. | 235/380 |
| 7,776,028 B2 | 8/2010 | Miller et al. | |
| 7,909,805 B2 | 3/2011 | Weston | |
| 2002/0115952 A1 | 8/2002 | Tumey | |
| 2002/0161346 A1 | 10/2002 | Lockwood et al. | |
| 2003/0040687 A1 | 2/2003 | Boynton et al. | |
| 2004/0030304 A1 | 2/2004 | Hunt et al. | |
| 2004/0073151 A1 | 4/2004 | Weston | |
| 2004/0243073 A1 | 12/2004 | Lockwood | |
| 2005/0203452 A1 | 9/2005 | Weston et al. | |
| 2005/0222527 A1 | 10/2005 | Miller et al. | |
| 2005/0222528 A1 | 10/2005 | Weston | |
| 2005/0222544 A1 | 10/2005 | Weston | |
| 2005/0261615 A1 | 11/2005 | Weston | |
| 2005/0261642 A1 | 11/2005 | Weston | |
| 2007/0239139 A1 | 10/2007 | Weston et al. | |
| 2008/0243044 A1 | 10/2008 | Hunt et al. | |
| 2009/0054855 A1 | 2/2009 | Blott et al. | |
| 2009/0177172 A1 | 7/2009 | Wilkes | |
| 2009/0312727 A1 | 12/2009 | Heaton | |
| 2010/0036367 A1 | 2/2010 | Krohn | |

FOREIGN PATENT DOCUMENTS

| | | |
|---|---|---|
| CA | 2551340 A1 | 5/1997 |
| CA | 2471780 A1 | 3/1999 |
| EP | 0 284 219 A | 9/1988 |
| EP | 1 088 569 A | 4/2001 |
| EP | 2 227 203 | 9/2010 |
| GB | 2 329 127 A | 3/1999 |
| GB | 2 356 148 A | 5/2001 |
| JP | H08-024344 | 1/1996 |
| JP | 2002-035133 | 2/2002 |
| JP | 2002-507435 | 3/2002 |
| WO | WO 88/02248 A | 4/1988 |
| WO | WO 91/00718 | 1/1991 |
| WO | WO 96/05873 | 2/1996 |
| WO | WO 97/33643 | 9/1997 |
| WO | WO 99/13793 | 3/1999 |
| WO | WO 01/34223 | 5/2001 |
| WO | WO 03/057071 A2 | 7/2003 |
| WO | WO 2005/105180 | 11/2005 |
| WO | WO 2008/041926 A1 | 4/2008 |
| WO | WO 2009/088757 A1 | 7/2009 |
| WO | WO 2009/088925 | 7/2009 |
| WO | WO 2009/088925 | 9/2009 |

OTHER PUBLICATIONS

U.S. Appl. No. 11/075,020, filed Mar. 8, 2005, Richard S. Weston, et al.
U.S. Appl. No. 11/095,859, filed Mar. 31, 2005, Miller et al.
U.S. Appl. No. 11/098,203, filed Apr. 4, 2005, Richard S. Weston.
U.S. Appl. No. 11/098,265, filed Apr. 4, 2005, Richard S. Weston.
U.S. Appl. No. 11/132,549, filed May 19, 2005, Richard S. Weston.
U.S. Appl. No. 11/064,813, filed Feb. 24, 2005, Weston, Richard S.
U.S. Appl. No. 11/874,021, filed Apr. 5, 2007, Weston et al.
Bagautdinov, "Variant of External Vacuum Aspiration in the Treatment of Purulent Diseases of Soft Tissues," Current Problems in Modern Clinical Surgery, 1986, 4 pages.
Boretos, John W., Cellular Polymers for Medical Use: The Vital Role of Porosity and Permeability, Cellular Polymers, 1984, vol. 3, pp. 345-358.
Chariker, M.E., et al, "Effective Management of Incisional and Cutaneous Fistulae with Closed Suction Wound Drainage," Contemporary Surgery. Jun. 1989, pp. 59-63, vol. 34 USA.
Eaglstein, W.H., et al., Wound Dressings: Current and Future, Clin. and Exper. Approaches to Dermal and Epidermal Repair: Normal and Chronic Wounds, 1991, 257-265.
Eisenbud, D.E., Modern Wound Management, Anadem Publishing, Chap. 16, 109-116, 1999.
International Search Report, International Application No. PCT/US07/074374, dated Mar. 27, 2008, in 6 pages.
International Preliminary Report, International Application No. PCT/US07/074374, dated Jan. 27, 2009, in 11 pages.
Jeter, Katherine F. ET, Managing Draining Wounds and Fistulae: New and Established Methods, Chronic Wound Care, Chapter 27, pp. 240-246, 1990.
Schein et al., "The 'Sandwich Technique' in the Management of the Open Abdomen," British Journal of Surgery, 1986, vol. 73, May, pp. 369-370.
U.S. Appl. No. 12/186,424, filed Aug. 5, 2008, Krohn.
Written Opinion dated Jan. 26, 2009 in application No. PCT/US07/74374 in 10 pages.
US 6,216,701, 04/2001, Heaton et al. (withdrawn)

* cited by examiner

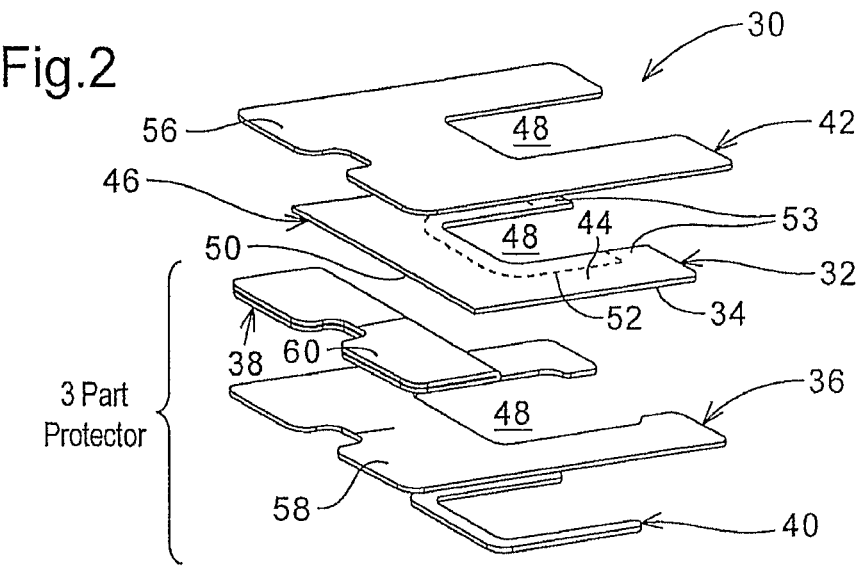
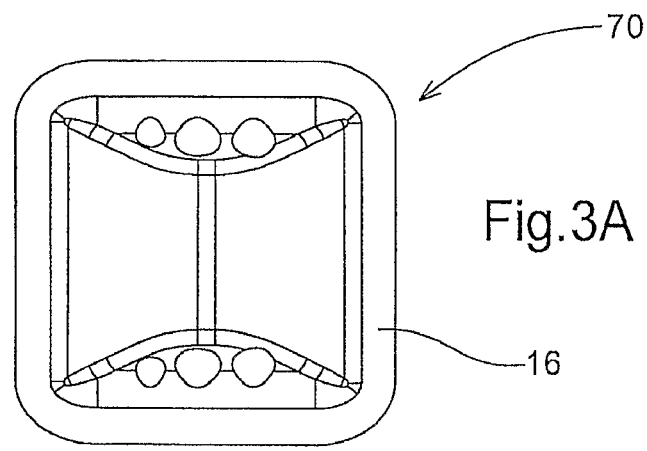
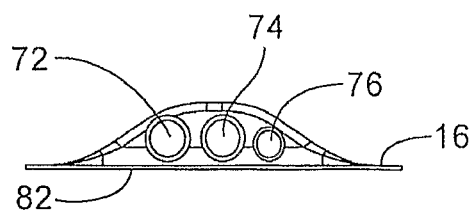
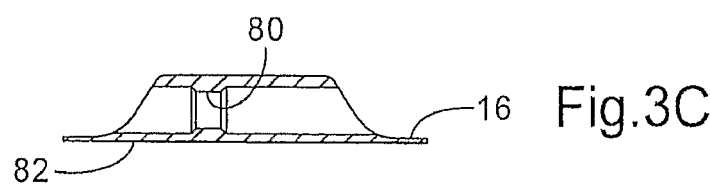

DRESSING

The present application claims priority to U.S. Provisional Application 60/833,553 filed Jul. 26, 2006 and Great Britain Application GB0712735.0 filed Jul. 2, 2007, both of which are hereby incorporated by reference in their entireties.

The present invention relates to wound dressings and more particularly, though not exclusively, to wound dressings used in topical negative pressure therapy (TNP) and to devices for sealing such dressings to conduits, tubes and the like passing in and/or out of a dressing covering the wound site.

Our co-pending International patent applications, WO 2004/037334, WO 2005/046760 and WO 2005/105180, describe inter alia and variously apparatus and methods for the treatment of wounds by aspiration, irrigation and cleansing, and are hereby incorporated by reference in their entireties. The apparatus and methods all involve in their most general aspects the covering of the wound site with a dressing which is sealed to the skin surrounding the wound by a flexible membrane type material through which or sealed thereto are conduits or tubes carrying fluids to the wound site and/or carrying wound exudates/fluids away from the wound site. The fluids may be liquids such as wound exudates and/or irrigation or cleansing fluids such as saline, for example, but may also be gases such as air, for example, used to aerate the wound site and to assist the liquid fluids away from the wound site by aspiration means.

The above referenced International patent applications all describe relatively complex systems for treating wounds by therapy usually involving a plurality of conduits needing to be sealed in respect of the dressing/wound site in order to preventing ress of ambient atmosphere into the wound site and to enable the apparatus to work effectively and efficiently without significant leakage.

Other less complex forms of apparatus are available which only apply TNP therapy to a wound and effectively there may be generally only one conduit or tube passing into the wound site.

Generally, conduits or tubes passing into the wound site are sealed to a flexible wound covering membrane or film by "pinching" the flexible covering around the conduit or tube so as to both stick the membrane material to the conduit or tube and also to itself to form a seal with the tube. Generally, the types of flexible membrane material used for wound coverings are provided with an adhesive layer such as a pressure sensitive adhesive, for example, in order for the material to adhere to the skin surrounding a wound. This method of sealing does not always work well and the seal around the conduit or tube degrades over time due to patient movements and adhesive-moisture interaction.

US2007/0032778, EP 1088569B show other types of connection devices and methods and are hereby incorporated by reference in their entireties. However, these mean that the patient is left with a moulding about in the centre of a wound that may cause pain and trauma if the patient lies upon it. Furthermore, such devices do not serve well for complex dressings such as those employing inflatable bladders, for example, or for small awkwardly sited wounds such as diabetic foot ulcers, for example.

Such methods of forming a seal with a conduit or tube are not always ideal. For example, sometimes it is desirable to be able to adjust the position of or extent of conduit or tube insertion into the wound site after the dressing has been adhered to the conduit or tube. This usually results in rupture or tearing of the flexible membrane which then needs to be repaired with additional material or the dressing replaced in its entirety.

The present invention has been devised to overcome failings of prior art methods of sealing conduits or tubes to dressings.

According to a first aspect of the present invention there is provided a grommet for locating and sealably receiving at least one flexible conduit having an end to be located within a dressing at a wound site, the grommet comprising at least one aperture therethrough for sealably receiving a conduit and a first face for contacting a patient's skin adjacent a wound.

The grommet may have an adhesive coating on the first face. The adhesive coating may be protected prior to use of the grommet by a protector layer comprising a known paper material, for example, impregnated or coated with a suitable material of low adhesion characteristic to the adhesive layer on the grommet such as silicone, for example.

The grommet may also be provided with a flange portion extending around at least a part of a body portion thereof so as to co-operate with a dressing to be described hereinbelow. The flange portion may extend completely around a body portion of the grommet.

The grommet according to the first aspect of the present invention may have a plurality of apertures therethrough to receive a plurality of conduits.

The first face of the grommet may be coated with an adhesive as discussed hereinbelow in more detail. However, the first face may be adhered to a patient's skin by means of a separate piece of drape backing material folded in two, for example, so that it has adhesive coated faces facing upwardly and downwardly; one face adhering to the first face of the grommet and the other face adhering to the patient's skin so as to adhere the grommet thereto.

According to a second aspect of the present invention, there is provided a dressing for use with a grommet member used to locate and retain conduits and/or tubes used in therapy of a wound, the dressing comprising a backing layer having an adhesive coating thereon for adhering the dressing to a patient; the backing layer having a cut-out therein for receiving a grommet member.

According to a third aspect of the present invention there is provided a combination of a dressing for use with a grommet member used to locate and retain conduits and/or tubes used in therapy of a wound, the dressing comprising a backing layer having an adhesive coating thereon for adhering the dressing to a patient; the backing layer having a cut-out therein for receiving a grommet member and, a grommet member having at least one aperture therethrough for receiving a conduit.

In the combination according to the third aspect of the present invention the grommet member preferably further comprises a flange portion extending around at least a part of a body portion of the grommet for attaching the grommet member to said adhesive coated backing layer.

The backing layer may be a thin flexible film material and comprise any suitable material known to those skilled in the art and may comprise one of the materials described in EP-A-0 751 757 which is hereby incorporated by reference in its entirety.

For example, the backing layer may comprise polyurethanes such as polyester or polyether polyurethanes and commercially available materials such as OPSITE (trade mark) or TEGADERM (trade mark). Desirably the backing material is initially supplied, as is well known in the art, having a protector layer adhered to the adhesive coated face and, preferably a support (sometimes referred to as a "carrier") layer on the reverse face to the adhesive coated face. The protector layer may again be any material known to those skilled in the art and silicone coated release paper is one example. The support layer may also be any suitable material known to those skilled in the art and suitable examples of which may include paper, foil or polymeric films. Preferably, the support layer is more strongly adhered to the backing layer than the protector layer so that the when the protector layer is peeled away the support layer remains to prevent any undesirable wrinkling of the backing layer, facilitate handling thereof and to maintain the generally 2-dimensional shape of the backing layer. Once the dressing has been adhered to the patient, the support layer may then be peeled away.

Suitable adhesives may be pressure sensitive adhesives which are well known to those skilled in the dressings art.

In a first embodiment of the dressing according to the present invention, the cut-out in the backing layer may be in the form of a bite out of one edge of the backing layer, effectively rendering the shape of the backing layer as a "horseshoe" form. It is preferred that the direction of the conduits in the grommet member may be aligned with and pass over the cut-out in the dressing edge.

In a second embodiment of the dressing according to the present invention, the cut-out may be an aperture in the backing layer leaving the backing layer as a ring form, for example, a square ring.

The apertured shape of backing layer is preferred since the grommet member is then supported entirely around its periphery and the adhesive layer on the backing layer is available for adhering the dressing to the patient around the entire periphery of the backing layer and grommet member thus enhancing the seal to the patient's skin of the dressing.

However, the horseshoe shaped backing layer is acceptable in that the grommet member is sealed against ambient atmosphere on the wound side. An advantage of this shape of dressing is that the patient's skin may be allowed to breath or vent sweat to the periphery from underneath the grommet member via the open edge. The grommet member is preferably formed from a soft polymeric plastics material. In some embodiments, the grommet member is also made from a stretchable material. Typically, the grommet member material may have a shore hardness in the range 55 A-70 A and easily conforms to a patient's contours, however, this hardness is not limiting and hardnesses outside this range may be perfectly suitable for use in the grommet member according to the present invention. Suitable materials for the grommet member include TPE, polyurethane, ethylvinylacetate, silicone, polyvinylchloride, for example. Furthermore, the grommet member is generally covered and additionally held down to the patients skin by an overlying adhesive drape material membrane which covers the whole of the wound site. Alternatively, as stated above, the grommet member may be provided with an adhesive coating on the face which contacts the patient's skin, the adhesive coated face being initially provided with a protector layer as with the backing layer. Thus the dressing and grommet member are completely sealed to the patient.

When the dressing is being attached to a patient's skin adjacent a wound, it is desirable that the grommet already has the required conduit or conduits installed to prevent any unnecessary additional distress or trauma to the patient. Attachment of conduits to the grommet member may be by the supplier and/or manufacturer of the grommet or may be threaded into the aperture by a care giver or clinician.

In the case of the dressing backing layer having a bite out of one edge, the protector and support layers may be easily removed from around the conduit or conduits. However, in the case of the backing layer having a closed aperture, it is necessary for the support layer to be cut in some manner in order to clear the conduit(s) when being removed. In this regard the support layer could be torn or cut with a pair of scissors, for example, but preferably all three layers are cut through one side during manufacture of the dressing.

The grommet member is provided with at least one aperture therethrough to receive a conduit or conduits. Where a plurality of conduits are required as in the treatment of wounds involving TNP therapy together with irrigation and/or cleansing as described in our co-pending International patent applications referred to hereinabove, separate apertures may be provided for each conduit or tube having a single lumen therethrough, for example. Alternatively, a single conduit having a plurality of lumens therethrough may be employed and the aperture through the grommet member may be suitably shaped, for example, as an elongate "flat" hole in cross section.

It is preferred that the at least one aperture through the grommet member is provided with sealing means to seal the conduit(s) which pass therethrough against leakage of fluid in use. Such sealing means preferably comprise flexible lip seals, "O" ring-type seals or sleeve-shaped seals which co-operate with the outer surface of the conduit(s). The provision of such lip seals render the conduit to grommet aperture interface leak-free and also reduces the force necessary to adjust the position of the conduit(s) in the grommet member when adhered to the patient with obvious benefit thereto.

In some embodiments, the grommet member and seal may be formed from relatively rigid material. Seals when made in a rigid form generally work as well as soft materials as the conduits employed are generally made from relatively soft and conformable material.

The dressing backing layer member and the grommet member may initially be supplied as two separate integers of the dressing of the present invention having the various protector and support layers as appropriate and the two integers then being assembled when being applied to the patient. However, it is preferred that the grommet member is attached to the backing layer at a manufacturing step in a manufacturing process.

Where the grommet member is supplied already adhered to the surrounding backing layer, the protector layer may be provided as a single piece covering the adhesive coated faces of both the backing layer and the grommet member, whether or not the latter is adhesively coated.

It is further preferred that the dressing may be supplied having the backing layer and grommet member joined and also having the appropriate conduit(s) already installed in the at least one aperture of the grommet member.

Where the backing layer and grommet member are supplied as two separate integers, the protector layer on the backing layer maybe provided in a plurality of portions, cut through and/or provided during a manufacturing process. For example, the protector layer adjacent the cut out portion may be in the form of a separately removable narrow border corresponding substantially to the width of the grommet member flange portion, this border portion being removed first to enable the grommet member to be initially adhered to the backing layer.

In known manner the protector layer may be formed of a plurality of portions to enable improved ease of handling and manipulation of the dressing when applying same to the patient. In this regard the protector layer may be arranged such that most of it is removed initially, so that the dressing may be conveniently and accurately positioned on the patient, whilst leaving a smaller, folded back portion of protector to be finally removed for the remainder of the adhesive coated backing layer to be adhered to the patient without the possibility of the adhesive layer being contaminated by the fingers of the clinician, for example, applying the dressing. After adhering the dressing to the patient, the support layer may be finally peeled away leaving the backing layer, grommet member with conduits in place. A final flexible drape covering of a known adhesive coated material such as OPSITE (trade mark), for example, may then be put in place substantially covering the adhered backing layer, the grommet member, the conduits situated within the wound site environment and the remainder of the wound area.

In a third embodiment of the dressing of the present invention, the backing layer may comprise two separate portions with the adhesive coated faces facing each other and the grommet member sandwiched between the two adhesive coated faces. In this embodiment a first portion of backing layer is effectively folded in two with protector layers on the outwardly facing adhesive coated faces. The protector layer from one of the two faces of the first portion is first removed and the exposed adhesive coated face is stuck to the patient's skin in a suitable position relative to the wound. The second piece of protector layer is then removed from the upwardly facing adhesive coated face and the grommet member then adhered to this second surface of the first portion. A second portion of backing material may then be placed to overlie the grommet member to sandwich it between the first and second backing layer portions. It is preferred that the length of the two backing layer portions is in the range from 1× to 5× the lateral width of the grommet member so that the excess length of each backing layer portion is sufficient to form a strong bond with each other either side of the grommet. The second portion may, if desired, also be folded in two so that the grommet member is sandwiched between the adhesive coated face of the first and second backing layer portions and the remaining upwardly facing face of the second portion is also adhesive coated. Thus, with the grommet member in place on the patient's skin, the second backing layer portion may be left with a piece of protector material on the upwardly facing adhesive coated face, which protector material may be finally peeled away immediately prior to the whole of the dressing and remaining wound area being covered with a flexible drape covering as in the preceding embodiments.

However, whilst the dressing referred to above has the first and second backing layer pieces in the length range 1× to 5×, they may, in fact, be much longer where, for example, the folded piece or pieces are laid across the diameter or width of a large wound.

However, it is not necessary in the third embodiment for the second portion of backing layer to be folded in two. The second portion of backing layer may be a single layer having the adhesive coated face protected with a protector layer and the reverse, non-adhesive coated face protected with a support layer as in the preceding embodiments. In this case the grommet member will be sandwiched between the adhesive coated faces of the first and second backing layers leaving the upwardly facing, non-adhesive coated face of the second backing layer portion protected by a support layer. The support layer may then be peeled away immediately prior to the dressing and the remainder of the wound site being covered with a flexible, adhesive coated film material which adheres to the upwardly facing face of the second backing layer portion to seal the grommet member against ingress of ambient air.

Examples of suitable materials for the backing layer for the dressings according to the present invention and also the overlying flexible drape film may be that known as OPSITE (trade mark) or TEGADERM (trade mark).

In the third embodiment of the dressing of the present invention the first and second backing layer portions may be supplied or provided as flat pieces of suitable material comprising backing layer, protector layer and support layer, the clinician then preparing same by peeling away protector layers, folding and adhering to the patient as necessary with the step of including the grommet member between the first and second backing layers. However, the dressing of the third embodiment may be provided in an assembled form with the grommet member being sandwiched between the two separate first and second portions of backing material with the outwardly facing faces having the appropriate protective protector layers or protector and support layers remaining in place for removal prior to adhering to a patient.

In the third embodiment, the second, upper backing layer portion may, in fact, be the overlying drape which covers the entire wound site.

In the third embodiment of a dressing according to the present invention, the grommet member may have a generally elliptical shape when viewed end on in a direction parallel to the axis of the at least one aperture therethrough.

The lateral ends of the grommet member used in the third embodiment may have the two outer surfaces thereof tapering into a fine edge with each other at each lateral end thereof so as to facilitate the joining of the first and second backing layer portions where they meet at each lateral end of the grommet member.

In the present invention the dressing is effectively sealed to the skin surrounding the wound by the overlying adhesively coated flexible drape film. However, the term "sealed" is not an absolute requirement or practically attainable since many flexible dressing membrane materials forming the wound cover are composed of semi-permeable plastics materials which are well known to those skilled in the art. Furthermore, there is almost inevitably some leakage between the skin and the sealing dressing material which is adhered thereto, usually by well known pressure sensitive adhesives, due to hairs and/or other skin surface irregularities and/or imperfections which are not easily completely sealed in absolute terms. The types of self adhesive, flexible dressing drape materials which are ordinarily used in TNP type therapy for sealing membranes over and around wounds are well know to those skilled in the art and will not be elaborated on further herein unless necessary.

Similarly as to the above with regard to the adhesive layer or coating on the flexible drape sealing film, there are very many suitable adhesives which may be used alternatively to pressure sensitive adhesives and include acrylic, silicone, stoma adhesives, hot melt adhesives and solvent spread adhesives, for example. The person skilled in the art will accordingly choose the most appropriate adhesive to the circumstances.

In order that the present invention may be more fully understood, examples by way of illustration only will now be described with reference to the accompanying drawings, of which:

FIG. 2 shows an exploded isometric view of a backing layer, protector and support layers according to a first embodiment of the present invention for use with the grommet member of the first example in FIG. 1 and alternatively with the grommet member of the second example in FIG. 3;

FIGS. 3A to 3C show a second example in plan view, end elevation and an axial cross section through the centre aperture, respectively of a grommet member for use in the dressing according to the present invention;

Figure 1A:
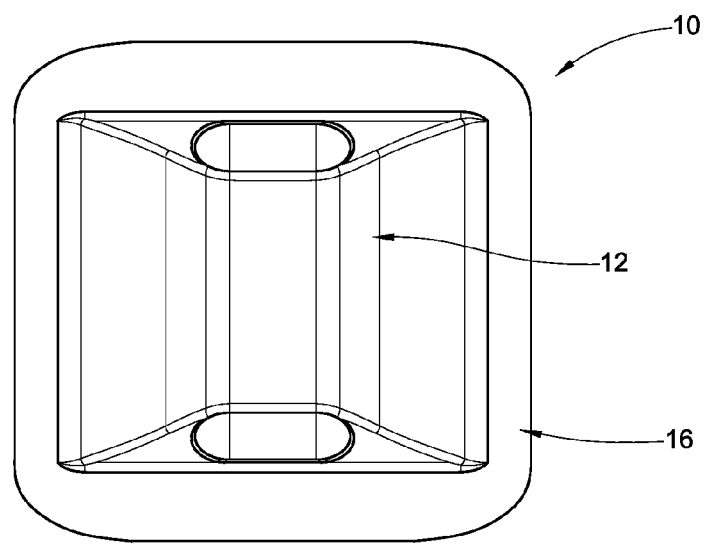
FIGS. 1A to 1C show a first example in plan view, end elevation and an axial cross section therethrough, respectively of a grommet member for use in the dressing according to the present invention.

Referring now to the drawings and where the same or similar features are denoted by common reference numerals.

Figure 1B:
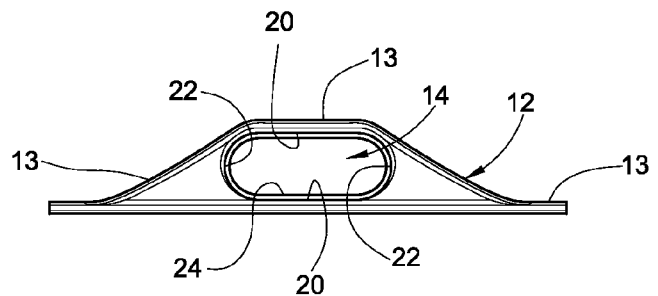
Figure 1C:
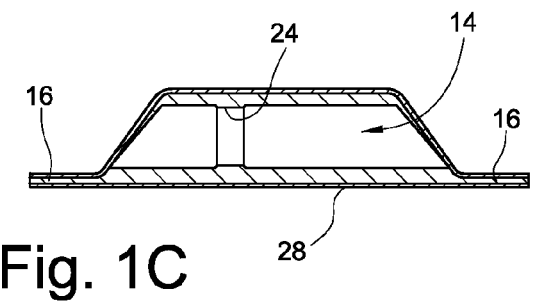

FIG. 1 shows a first example of a grommet member 10 which may be used in the dressing according to the present invention. The grommet member comprises a body portion 12 having an aperture 14 therethrough and a flange portion 16 surrounding the body portion 12. The grommet member is made of a soft, conformable plastics material such as TPE, polyurethane, ethylvinylacetate, silicone, polyvinylchloride, for example. The central aperture 14 is a flattened hole having two parallel sides 20 and two semi-circular ends 22 and is formed to receive a single correspondingly shaped conduit (not shown) of co-operative outer form and size and having a plurality, e.g. three lumens (also not shown) therethrough. The aperture 14 is further provided with an internal lip seal 24 around the periphery for sealing against the outer surface of the conduit. The provision of the lip seal allows the conduit to slide more easily with less force through the aperture 14 when being adjusted due to less frictional stick/slip phenomena whilst still being fully sealed against leakage of fluid out and ingress of ambient air into the wound site (not shown). The lower face 28 and/or top face 13 of the grommet member may be provided with an adhesive coating, e.g. Stoma Adhesive, for sticking directly to a patient's skin (not shown) in which case the grommet may initially be provided with a protector layer (not shown) which would be removed when applying to a patient. An adhesive coating on the partially domed top face 13 may be to assist adhesion thereto of an overlying drape material (not shown) covering the entire wound area.

The grommet member of FIG. 1 may be used with the adhesive dressing component shown in FIG. 2 (as may the grommet member of FIG. 3). The dressing component 30 shown in FIG. 2 initially comprises (prior to adhering to a patient) a backing layer 32 having an adhesive coating 34 on one face 46; a three-part protector layer 36, 38, 40 adhered to the adhesive coating 34; and, a support layer 42 adhered to the non-adhesively coated face 44 of the backing layer 32. The three-part protector layer comprises a main portion 36 which extends over most of the adhesive coated face 46 except for a relatively smaller area 50 at an end of the dressing component opposite to a cut-out 48 which is to receive the grommet member 10 (or grommet member 70, see FIG. 3 below). The smaller area 50 is initially protected by a second, folded portion 38 of protector material, which remains after the main portion 36 is removed, so as to protect the smaller area 50 from contamination by a clinician's fingers (not shown), for example. The third portion of protector material 40 protects a narrow border 52 (indicated by a dashed line) of adhesive coating surrounding the cut-out 48 except for a small portion 53 adjacent each side of the mouth of the cut-out portion 48 which remains to hold the front edge of the grommet member down to the patient's skin. The support layer 42, main portion of protector layer and second, folded portion of the protector layer are all provided with extension tabs 56, 58, 60, respectively to aid easy grasping with the finger tips and facilitate peeling away of these layers.

In use (where the grommet member 10 is not already adhered to the dressing component 30) the narrow protector layer 40 is peeled away from the adhesive coated face 46 to expose the border portion 52 of adhesive. The grommet member 10 is then entered into the cut out portion 48 such that the upper surface of the flange portion 16 of the grommet is adhered to the border 52 on three sides (note that at this stage the required conduits have already been inserted into the aperture 14). The dressing assembly 10, 30 is then adhered to a patient in a suitable position adjacent a wound (not shown) which is achieved by peeling away the protector layer main portion 36 (and any protector layer that the grommet member may have on its lower surface if it has an adhesive coating). The combined dressing components 10, 30 are then positioned over the desired position on the patient and pressed down in place, the rear end of the dressing at area 50 then being lifted slightly to enable the second, folded portion 38 of the protector layer to be removed and area 50 of the backing layer 32 then pressed down onto the patient's skin. Finally, the upper support layer 42 may then be peeled away to leave the dressing in place. Normally, a further flexible self-adhesive drape covering (not shown but see FIG. 6 below) will be placed over the entire wound area to provide a sealed region around the wound site suitable for the application of TNP therapy, irrigation, cleansing or other therapy via the conduit(s) as appropriate.

The provision and methods of manufacture of the various layers and constituent portions described above and in succeeding embodiments will be well known to those skilled in the art. The small protective layer 40 may be separated from the main portion by a "kiss cut", for example, on a strip of material having a plurality of such dressing components passing through a manufacturing machine.

FIGS. 3A to 3C show views of a second example of a grommet member 70 suitable for use with a dressing according to the present invention. The grommet member is essentially similar to that shown in FIG. 1 except for the provision of three apertures 72, 74, 76 each aperture being provided with lip seal features 80 (only the lip seal in the central aperture 74 is shown). In this case two of the apertures 72, 74 are substantially the same diameter whilst the third aperture 76 is smaller to accommodate different sized conduits. As in the first example of FIG. 1, a flange portion 16 is provided for adhering to a dressing component (30 in FIG. 2 or 90 in FIG. 4 below). The lower face 82 of the grommet member may be provided with an adhesive coating in which case it will also be provided with a protector layer (both not shown).

Figure 4A:
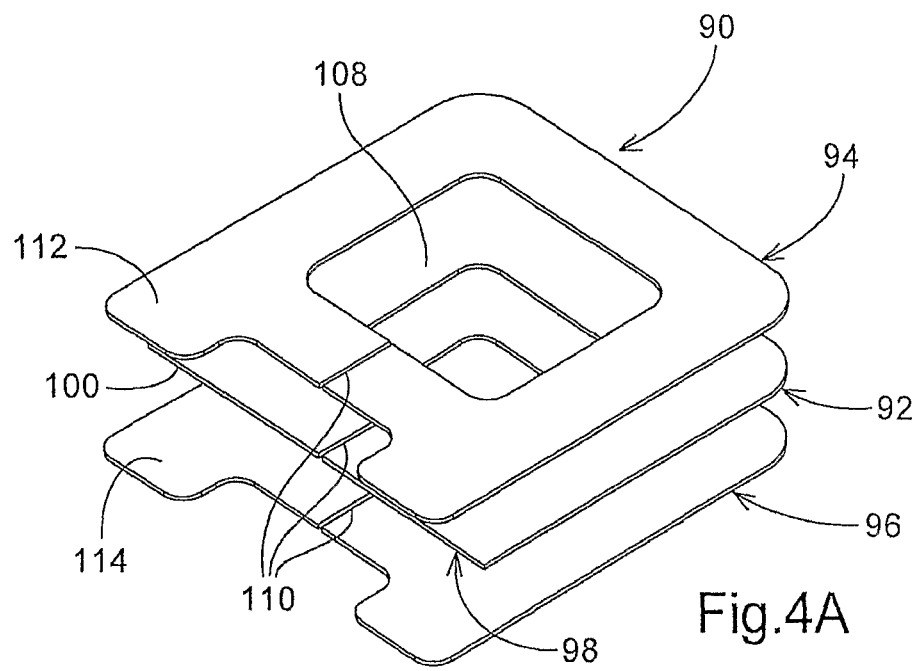
FIGS. 4A and 4B show an exploded isometric view of a backing layer, protector and support layers; and a plan view of a dressing according to a second embodiment of the present invention for use with either of the grommet members of FIG. 1 or 3.
Figure 4B:
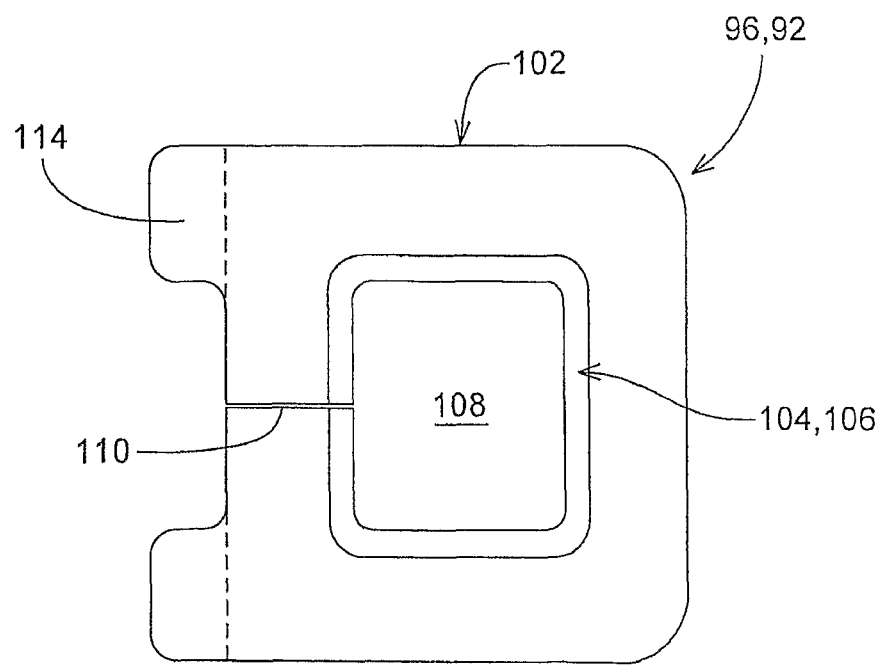

A dressing component 90 of a second embodiment of the present invention is shown in FIGS. 4A and 4B and which component may be used with equal facility with either of the grommet members of FIGS. 1 and 3. In this embodiment, there is a backing layer 92; a support layer 94; and, a protector layer 96. The backing layer has a lower face 98 having an adhesive coating 100 whilst the protector layer 96 is divided into a main portion 102 and a narrow portion 104 which surrounds and protects the adhesive coated border portion 106 of a central cut-out 108 which is a closed aperture surrounded on all four sides by the adhesive coated backing layer 92. FIG. 4B shows the narrow border portion 104, 106 more clearly. This embodiment has a closed aperture 108 and which is provided with a slit 110 to enable the conduits (not shown) installed in the grommet member to be easily cleared. The support and protector layers are again provided with tabs 112, 114, respectively which extend beyond the adhesive coated surface 98 of the backing layer to facilitate handling and placing of the dressing.

The backing layer 92 does not need to have the slit 110 therein as this layer remains on the patient. The slit 110 may, however, facilitate manufacture of the dressing 90.

The dressing component 90 of the second embodiment may be used with either of the grommet members 10, 70 described hereinabove. In use, in essentially the same way as with the dressing component 30 of FIG. 2, the adhesive coating of the narrow border 106 may be exposed by removal of the small protector layer 104 and adhered to the upper surface of the flange portion 16 of the grommet member. The main portion 102 of the protector layer and any protector layer on the grommet member lower face is then removed and the dressing positioned over the desired place on the patient and pressed down into position. The support layer 94 is finally removed and the dressing over the whole wound area finally completed as described above. The slits 110 facilitate removal of the various layers and also placement of the initial dressing component 90 over the conduits in the grommet member.

The second embodiment of the dressing according to the present invention is considered to have the advantage that the grommet member is held down to the patient's skin along all four edges of the flange portion thus further reducing the possibility of any leakage either inwardly or outwardly of the dressing.

The second embodiment also substantially removes the need for the grommet member to have an adhesive coating on its lower face.

The above embodiments comprising grommet members 10 or 70 and dressing components 30 or 90 as desired may be put into effect at a manufacturing stage whereby the grommet member 10 or 70 is pre-adhered to the dressing component 30 or 90 during manufacture. In this way the protective layer may be made into a single piece which extends over substantially the whole of the adhesive coated area including the lower face of the grommet member which may or may not be adhesive coated. The pre-assembled dressing may also be provided with suitable conduits and the whole assembly packaged in a sealed bag and sterilised by known techniques.

Figure 5A:
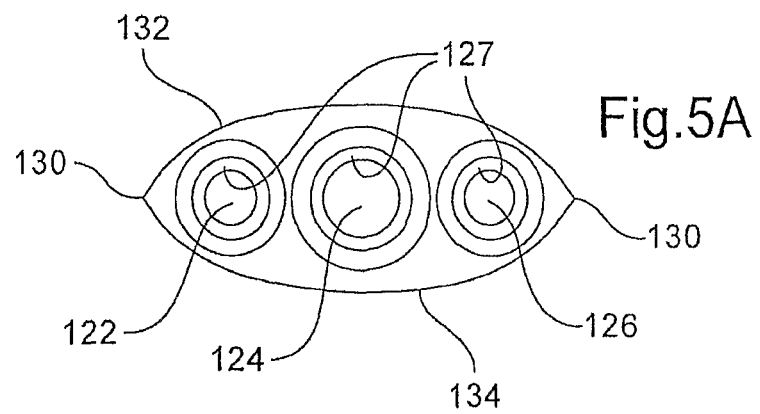
FIGS. 5A, 5B and 5C show an end elevation view, an isometric view and a side elevation, respectively of a grommet member for use in a third embodiment of a dressing according to the present invention.
Figure 5B:
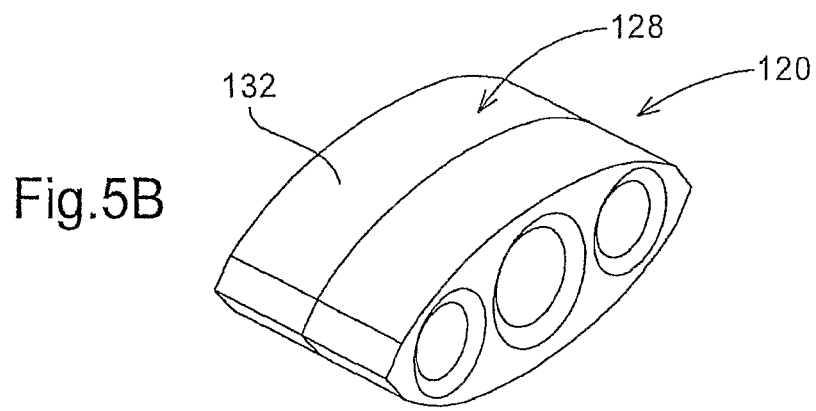
Figure 5C:
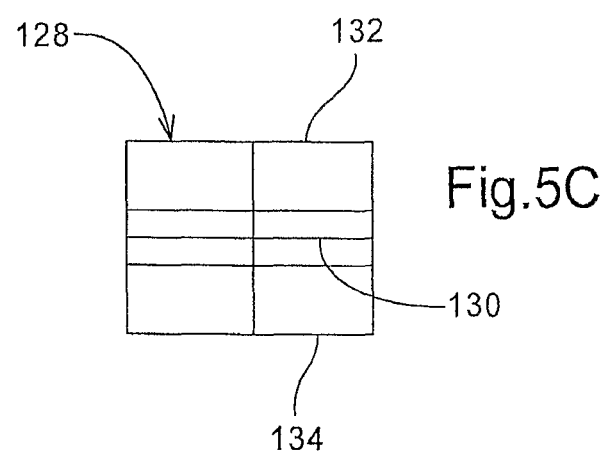

FIG. 5 shows a third embodiment of a dressing grommet member 120. In this embodiment, the grommet member is of generally elliptical shape when viewed in end-on elevation in a direction parallel to the aperture axes and comprises three separate apertures 122, 124, 126 for receiving conduits (not shown); all apertures being provided with lip seal features 127 in the bores thereof. The body 128 of the grommet member has at each lateral extremity a fine tapered edge 130 wherein the upper 132 and lower 134 surface are blended in to each other to facilitate the joining and adhesion of the accompanying dressing components 142, 144 to be described below with respect to FIG. 6. The grommet member 120 of the third embodiment may, for example, be made by moulding from a polyurethane material or from a relatively more rigid material such as polyethylene or polypropylene, for example.

Figure 6A:
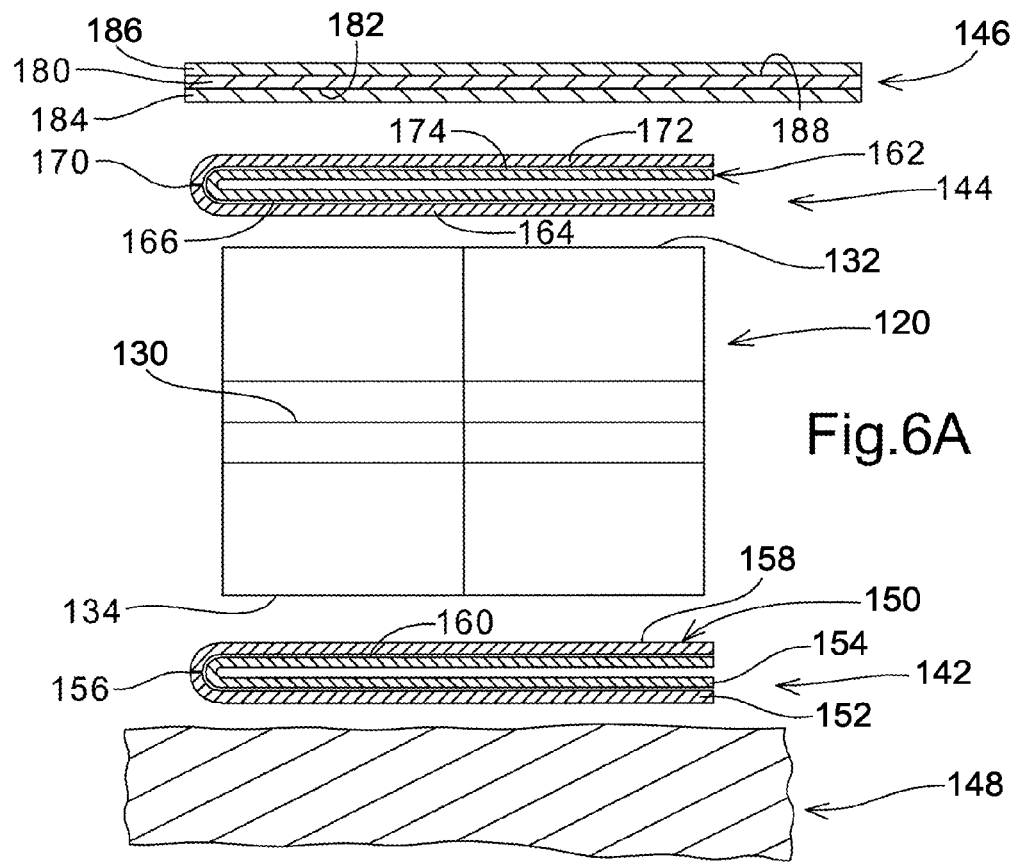
FIGS. 6A and 6B show cross sections through two alternative constructions of the third embodiment of a dressing according to the present invention adhered to a patient's skin.

FIG. 6A shows a first example of a dressing in exploded form, wherein the backing layers still have protector and support layers as appropriate, according to the third embodiment of the present invention and utilising the grommet member 120 of FIG. 5. The grommet member is shown at 120; a first backing layer portion at 142; a second backing layer portion at 144; an overlying flexible drape film at 146; and a portion of patient's skin/flesh at 148 (note that the overlying drape film 146 does not form part of the dressing of the present invention per se). The first backing layer portion 142 comprises a strip of suitable adhesive coated material 150 such as OPSITE (trade mark), for example, of significantly greater length than the lateral width of the grommet 120, for example, at least 3× so that there is an appreciable overlap at each end of the grommet member, folded back on itself so that when the lower protector layer 152 is removed an adhesive coated face 154 faces the patient's skin 148. Removal of the lower piece of protector material 152 is facilitated by the protector layer being kiss cut at 156 during manufacture. This adhesive coated face 154 is then pressed down on the patient's skin 148 and the upper piece of protector layer 158 removed to expose the adhesive coated face 160 of the backing layer 142. The grommet member lower surface 134 is then stuck down to this adhesive surface 160. The second backing layer 144 is also similarly constructed from a folded strip 162 of suitable material. The lower piece of protector layer 164 is first removed to expose the lower adhesive coated face 166 of the strip 162 which is stuck down to the upper surface 132 of the grommet member 120 and the lateral ends of the adhesive coated surfaces 160, 166 (not shown) either side of grommet member are stuck to each other to effectively seal the grommet member between the two backing layers 142, 144, the seal at the lateral ends of the grommet member being facilitated by the tapered ends 130 thereon. Again, removal of the lower piece of protector material is facilitated by a kiss cut 170 on the second backing layer. The upper piece of protector material 172 on the second backing layer may then be removed to expose an upper adhesive coated face 174 ready to receive an overlying flexible drape material layer 146. The overlying drape material may again be made from OPSITE (trade mark) material, for example, and may cover the entire area of the wound and the dressing according to the present invention. The drape material has a backing layer 180 having an adhesive coated face 182; a protector layer 184 on the adhesive coated face; and, a support layer 186 adhered to the non-adhesive coated face 188 of the backing layer 180. Thus when the protector layer is removed the adhesive coated face 182 and the adhesive coated face 174 of the second backing layer are brought into contact with each other to seal the dressing of the present invention to the wound site environment.

Optionally the backing layer portions 144 and 142 may have a support layer (not shown) which can be removed at the end of the application of the backing layer 144.

The kiss cut 156 is optional since it is possible to remove the protector material layers 152, 158 as one but handling is less easy without the cut 156.

Figure 6B:
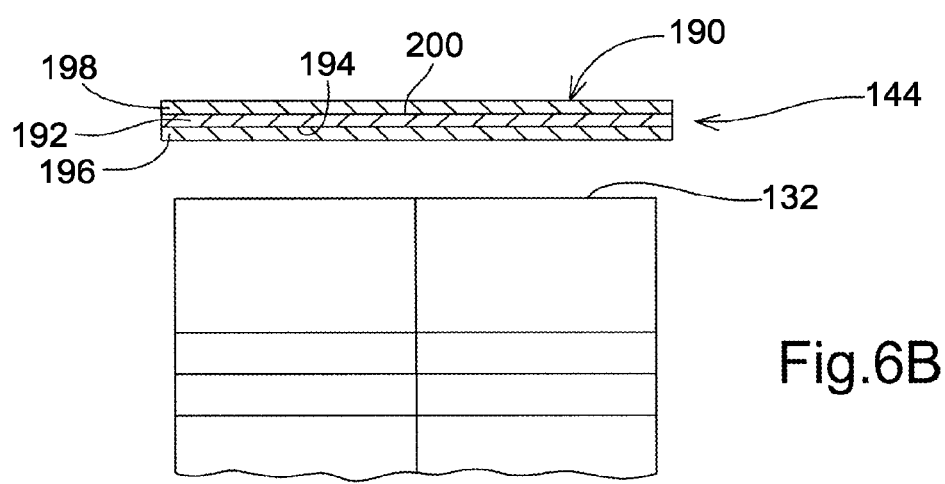

A modified example of the third embodiment is shown in FIG. 6B where the second backing layer 144 is changed for a strip of suitable material 190 which has a backing layer 192 having an adhesive coated face 194; a protector layer 196; and, a support layer 198. The remainder of this modified embodiment may be the same in all material respects to the embodiment shown in FIG. 6A. The assembly method steps may be the same except that when the support layer 198 is removed only the plain, non-adhesive coated backing layer material faces upwardly. However the adhesive coated face 182 of the overlying drape material adheres well to the surface 200 when the support layer 198 is removed.

An advantage of using the backing layer 144 as shown in FIG. 6B, even where a subsequent drape covering the entire wound area and grommet member 120 is applied, is that it keeps the grommet member secure and in position whilst the remainder of the dressing is applied and/or manipulated.

The third embodiments of FIGS. 6A and 6B may be modified by changing the backing layer and adhesive face options to any combination above and below the grommet member which best deals with a particular wound or situation.

Figure 7A:
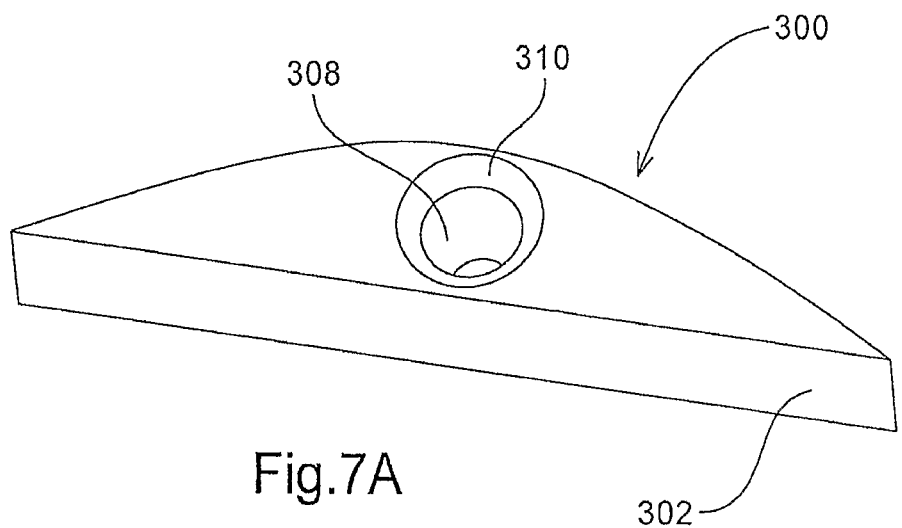
FIGS. 7A and 7B show a further embodiment of a grommet according to the first aspect of the present invention from two perspectives.
Figure 7B:
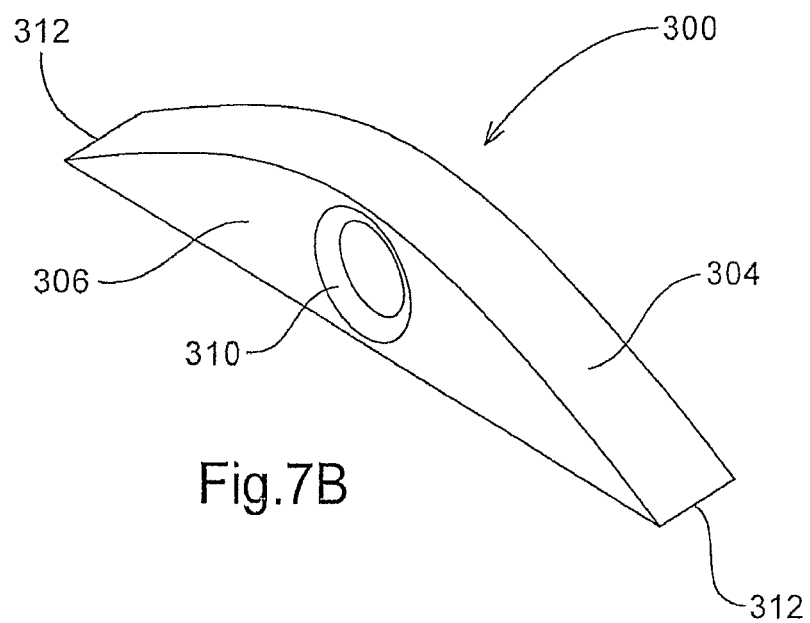

FIGS. 7A and 7B show a fourth embodiment of a grommet member 300 according to the first aspect of the present invention. The grommet member 300 comprises a flat lower first face 302 for contact with a patient's skin (not shown); a partially domed, or curved, upper second face 304; two planar faces 306 and an aperture 308 therethrough for receiving a conduit (not shown). The aperture 306 has a tapered lead-in 310 to facilitate threading a conduit through the aperture whilst the aperture itself forms a sleeve-seal with a co-operating conduit. The lower face 302 may be coated with an adhesive layer to assist adherence of the grommet member to a patient's skin. The lower face also having a protective layer of a suitable material such as a silicone coated release paper (not shown) when so adhesive coated. The lower face 302 at lateral ends thereof meet lateral ends of the upper or second face 304 at feather edges 312. Alternatively, the grommet member may be employed in a dressing structure as described with reference to FIGS. 6A and 6B as described hereinabove the tapering edges 312 making the grommet particularly suitable for such a dressing structure.

Figure 8A:
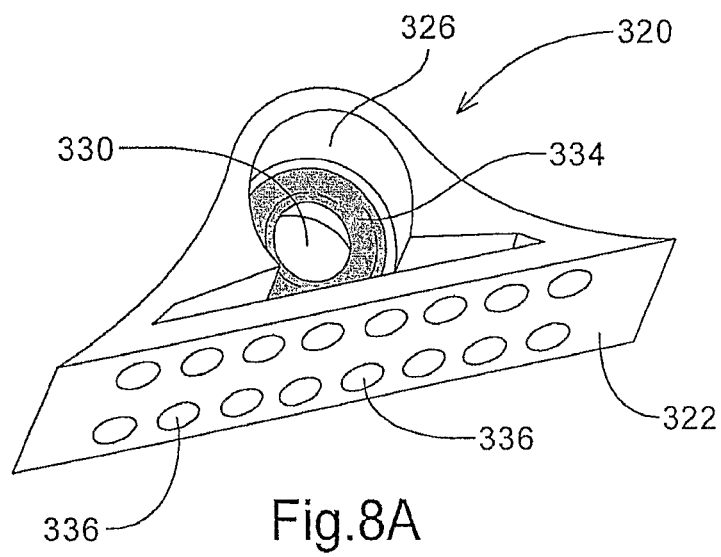
FIGS. 8A and 8B which show a yet further embodiment of a grommet according to the first aspect of the present invention from two perspectives.
Figure 8B:
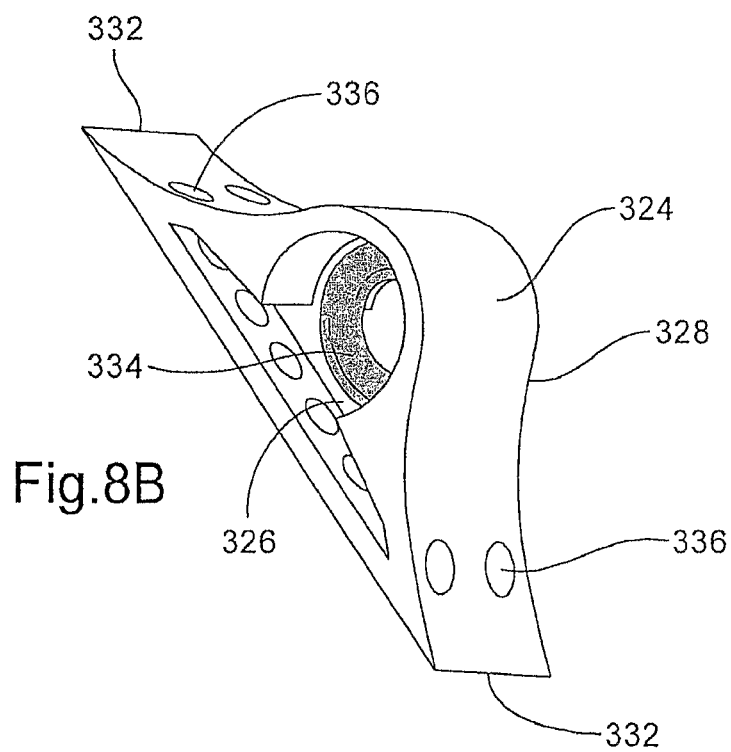

FIGS. 8A and 8B show a fifth embodiment of a grommet member 320 according to the first aspect of the present invention. The grommet member 320 comprises a lower flat first face 322 for contact with a patient's skin (not shown); a partially domed, or curved, upper second face 324; recessed front and rear faces 326, 328, respectively; and an aperture 330 therethrough. The upper, second face 324 and lower first face 322 meet at lateral ends thereof at feather edges 332. The lower flat face 322 may be coated with an adhesive layer as described hereinabove (or, again may be employed as part of a dressing structure as exemplified by FIG. 6 and the accompanying description). The aperture 330 has a sealing member 334 in the form of an "O" ring seal therein for sealing with a co-operating conduit. The "O" ring seal member 334 has an inner diameter that is slightly smaller than the conduit's external diameter so that an effective seal is formed when the conduit is threaded through the "O" ring seal member 334. The conduit can be threaded through the aperture 330 and "O" ring seal member from the flat side of the grommet member 320. The "O" ring seal member 334 may be formed integrally from the same material as the grommet 320 or may be included by an insert moulding technique and utilise a different material. An array of ventilation holes 336 is provided to enable a patient's skin to breath and prevent maceration thereof. The recessed front and rear faces 326, 328 make this embodiment of a grommet member particularly flexible and accommodating should the patient lie on the grommet member.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The invention claimed is:

1. A dressing apparatus comprising:
   a grommet member for locating and sealably receiving at least one conduit at or near a wound site, the wound site surrounded by healthy skin defining a first plane, the grommet member comprising a body portion comprising:
      a lower face for contacting the healthy skin adjacent the wound site;
      a partially domed upper face for attaching the grommet member to a dressing member;
      front and rear faces connecting the lower face with the upper face;
      at least one aperture extending through the front and rear faces along a longitudinal axis in a direction generally parallel with the first plane, the at least one aperture configured to receive the at least one conduit such that the at least one conduit is slidable through the aperture, wherein the at least one aperture defines an enclosed cross-section along a length of the at least one aperture; and
      a seal around a periphery of the at least one aperture configured to seal against an outer surface of the at least one conduit.

2. The dressing apparatus of claim 1, wherein the lower face is substantially flat.

3. The dressing apparatus of claim 1, wherein the seal comprises one of a lip seal and an "O" ring seal.

4. The dressing apparatus of claim 1, wherein the seal has a length along the length of the at least one aperture that is less than the length of the at least one aperture through the body portion.

5. The dressing apparatus of claim 1, wherein the seal has an inner diameter that is less than an inner diameter of the at least one aperture.

6. The dressing apparatus of claim 1, wherein the grommet member further comprises a flange portion surrounding the body portion.

7. The dressing apparatus of claim 6, wherein the body portion and the flange portion are integrally formed.

8. The dressing apparatus of claim 1, wherein a direction of the at least one conduit received by the grommet member is substantially parallel to the first plane.

9. The dressing apparatus of claim 1, wherein the upper face is curved.

10. The dressing apparatus of claim 1, wherein the lower face is provided with an adhesive thereon, the adhesive configured to adhere the lower face to the healthy skin of the patient.

11. The dressing apparatus of claim 10, wherein the lower face is provided with a release paper layer configured to protect the adhesive prior to use.

12. The dressing apparatus of claim 10, wherein the adhesive comprises a folded strip having an adhesive coated face.

13. The dressing apparatus of claim 1, wherein the lower face is substantially planar.

14. The dressing apparatus of claim 1, wherein the at least one aperture has a tapered lead-in to facilitate sliding of the at least one conduit through the aperture.

15. The dressing apparatus of claim 1, wherein the lower face comprises a plurality of ventilation holes.

16. The dressing apparatus of claim 1, wherein the front and rear faces each comprise a recessed portion where the at least one aperture extends through the front and rear faces.

17. The dressing apparatus of claim 1, wherein the at least one aperture is configured to receive the at least one conduit such that a portion of the at least one conduit extends beyond the grommet member having an end positioned within the wound site.

18. The dressing apparatus of claim 17, wherein the at least one conduit movably engages the at least one aperture such that an extent or position of the portion of the at least one conduit positioned within the wound site is adjustable.

19. The dressing apparatus of claim 1, wherein the front and rear faces have a generally elliptical shape when viewed in a direction parallel to the longitudinal axis.

20. The dressing apparatus of claim 19, wherein the upper face and the lower face of the body portion of the grommet member meet each other at a tapered edge.

21. The dressing apparatus of claim 1, wherein the grommet member comprises a plurality of apertures therethrough.

22. The dressing apparatus of claim 21, wherein at least two of the apertures are of different sizes.

23. The dressing apparatus of claim 1, further comprising a conduit advanceable through the at least one aperture.

24. The dressing apparatus of claim 1, further comprising a flexible drape configured to cover the wound site and at least a portion of the grommet member.

25. The dressing apparatus of claim 1, further comprising a wound packing material configured to be positioned between a wound and a wound cover.

26. The dressing apparatus of claim 23, further comprising a collection reservoir configured to collect exudate from a wound through the at least one conduit.

27. The dressing apparatus of claim 1, further comprising a source of negative pressure in communication with at least one of a collection canister and a conduit advanceable through the at least one aperture.

28. The dressing apparatus of claim 6, further comprising a dressing member, wherein the dressing member is configured to be positioned over the wound site, the dressing member comprising a backing layer having adhesive on at least a first surface thereof.

29. The dressing apparatus of claim 28, wherein the upper face of the grommet member is configured to be sealably secured to the adhesive first surface of the backing layer.

30. The dressing apparatus of claim 28, wherein the backing layer further comprises one or more extension tabs.

31. The dressing apparatus of claim 28, further comprising a first protector layer releasably secured to the first surface of the backing layer.

32. The dressing apparatus of claim 31, further comprising a second protector layer releasably secured to the first surface of the backing layer.

33. The dressing apparatus of claim 28, wherein the dressing apparatus is configured so that the dressing member extends beyond an outer edge of the grommet member on three sides of the grommet member.

34. The dressing apparatus of claim 28, wherein the dressing member comprises a cutout in the backing layer, wherein the grommet member is positioned relative to the dressing member so that the body portion of the grommet member is positioned in the cutout.

35. The dressing apparatus of claim 34, wherein the cutout is positioned along a peripheral edge of the backing layer.

36. The dressing apparatus of claim 35, wherein
the adhesive is configured to adhere to the flange portion so as to secure the grommet member to the backing layer;
the adhesive is also configured to adhere to the healthy skin adjacent to the wound site so as to secure the dressing to the healthy skin; and
a protector layer is removably secured to at least a portion of the first adhesive surface of the backing layer, the protector layer being configured to be removed from the dressing member before the dressing member is secured to the healthy skin adjacent to the wound.

37. The dressing apparatus of claim 15, further comprising:
a flexible drape film;
a first backing layer portion configured to be positioned between the grommet member and a patient's skin, the first backing layer comprising an adhesive coated folded strip of material, a lower protector layer and an upper protector layer; and
a second backing layer portion configured to be positioned between the grommet member and the flexible drape film, the second backing layer comprising an adhesive coated folded strip of material, a lower protector layer and an upper protector layer.

* * * * *

UNITED STATES PATENT AND TRADEMARK OFFICE
CERTIFICATE OF CORRECTION

| | | |
|---|---|---|
| PATENT NO. | : 8,784,393 B2 | Page 1 of 1 |
| APPLICATION NO. | : 12/375191 | |
| DATED | : July 22, 2014 | |
| INVENTOR(S) | : Richard Scott Weston et al. | |

It is certified that error appears in the above-identified patent and that said Letters Patent is hereby corrected as shown below:

In the Specification

At column 1, line 31-32, change "preventingress" to --prevent ingress--.

At column 6, line 42, change "well know" to --well known--.

Signed and Sealed this
Fourteenth Day of April, 2015

Michelle K. Lee
*Director of the United States Patent and Trademark Office*